United States Patent
Kim et al.

(10) Patent No.: US 9,695,294 B2
(45) Date of Patent: Jul. 4, 2017

(54) EPOXY RESIN COMPOSITION FOR ENCAPSULATING SEMICONDUCTOR DEVICE AND SEMICONDUCTOR DEVICE ENCAPSULATED USING THE SAME

(71) Applicants: Min Gyum Kim, Uiwang-si (KR); Seung Han, Uiwang-si (KR); Hwan Sung Cheon, Uiwang-si (KR)

(72) Inventors: Min Gyum Kim, Uiwang-si (KR); Seung Han, Uiwang-si (KR); Hwan Sung Cheon, Uiwang-si (KR)

(73) Assignee: Cheil Industries, Inc., Gumi-Si, Kyeongsangbuk-do (KR)

( * ) Notice: Subject to any disclaimer, the term of this patent is extended or adjusted under 35 U.S.C. 154(b) by 114 days.

(21) Appl. No.: 14/140,607

(22) Filed: Dec. 26, 2013

(65) Prior Publication Data

US 2014/0179835 A1 Jun. 26, 2014

(30) Foreign Application Priority Data

Dec. 26, 2012 (KR) .................. 10-2012-0153915

(51) Int. Cl.

| | | |
|---|---|---|
| C08G 59/04 | (2006.01) |
| C08G 59/62 | (2006.01) |
| C08L 63/00 | (2006.01) |
| C07F 9/28 | (2006.01) |
| C07F 9/54 | (2006.01) |
| C07F 9/6571 | (2006.01) |
| C08K 3/36 | (2006.01) |
| C08K 3/00 | (2006.01) |
| H01L 23/29 | (2006.01) |

(52) U.S. Cl.
CPC ............... C08K 3/36 (2013.01); C07F 9/28 (2013.01); C07F 9/54 (2013.01); C07F 9/6571 (2013.01); C08G 59/04 (2013.01); C08G 59/62 (2013.01); C08K 3/0033 (2013.01); C08L 63/00 (2013.01); H01L 2924/0002 (2013.01)

(58) Field of Classification Search
CPC ....................................................... C08K 3/36
See application file for complete search history.

(56) References Cited

U.S. PATENT DOCUMENTS

2006/0009547 A1* 1/2006 Maeshima ........... C07D 301/14
                                                              523/427
2007/0027273 A1* 2/2007 Murotani ............. C08G 59/621
                                                              525/481

FOREIGN PATENT DOCUMENTS

| CN | 102112517 A | 6/2011 |
| CN | 102190864 A | 9/2011 |
| CN | 102690620 A | 9/2012 |
| JP | 2007-224229 A | 9/2007 |
| JP | 2007224229 A * | 9/2007 |
| JP | 2011-184490 A | 9/2011 |
| JP | 2011184490 A * | 9/2011 |
| JP | 2011202038 A * | 10/2011 |

OTHER PUBLICATIONS

Office Action mailed Aug. 13, 2015 in corresponding Chinese Patent Application No. 201310728096.9.
Office Action mailed Mar. 23, 2016 in corresponding Chinese Patent Application No. 201310728096.9.

* cited by examiner

Primary Examiner — Randy Gulakowski
Assistant Examiner — Ha S Nguyen
(74) Attorney, Agent, or Firm — Lee & Morse, P.C.

(57) ABSTRACT

An epoxy resin composition includes: an epoxy resin; a curing agent; a curing accelerator; and an inorganic filler, wherein the curing accelerator includes a 4-valent ammonium salt or a 4-valent phosphonium salt represented by Formula 1,

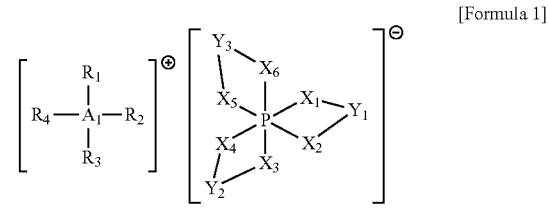

[Formula 1]

wherein $A_1$ is nitrogen or phosphorus; $R_1$, $R_2$, $R_3$ and $R_4$ are each independently a substituted or unsubstituted $C_1$ to $C_{30}$ hydrocarbon group, or a substituted or unsubstituted $C_1$ to $C_{30}$ hydrocarbon group including a hetero atom; $X_1$, $X_2$, $X_3$, $X_4$, $X_5$ and $X_6$ are each independently an oxygen atom (O), a sulfur atom (S), or NH; and $Y_1$, $Y_2$ and $Y_3$ are each independently a substituted or unsubstituted $C_1$ to $C_{30}$ hydrocarbon group, or a substituted or unsubstituted $C_1$ to $C_{30}$ hydrocarbon group including a hetero atom.

5 Claims, No Drawings

EPOXY RESIN COMPOSITION FOR ENCAPSULATING SEMICONDUCTOR DEVICE AND SEMICONDUCTOR DEVICE ENCAPSULATED USING THE SAME

CROSS-REFERENCE TO RELATED APPLICATION

Korean Patent Application No. 10-2012-0153915, filed on Dec. 26, 2012, in the Korean Intellectual Property Office, and entitled: "Epoxy Resin Composition For Encapsulating Semiconductor Device and Semiconductor Device Encapsulated Using The Same," is incorporated by reference herein in its entirety.

BACKGROUND

1. Field

Embodiments relate to an epoxy resin composition and a semiconductor device encapsulated using the same.

2. Description of the Related Art

Transfer molding of an epoxy resin composition may be used as a method for packaging semiconductor devices, e.g., ICs, LSIs, and the like due to low cost and ease of mass production.

SUMMARY

Embodiments are directed to an epoxy resin composition that includes: an epoxy resin; a curing agent; a curing accelerator; and an inorganic filler, wherein the curing accelerator includes a 4-valent ammonium salt or a 4-valent phosphonium salt represented by Formula 1:

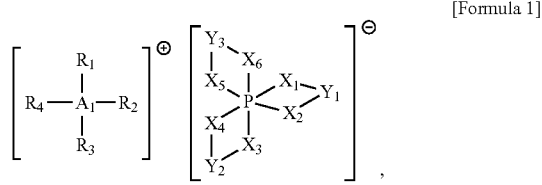

[Formula 1]

wherein $A_1$ is nitrogen or phosphorus; $R_1$, $R_2$, $R_3$ and $R_4$ are each independently a substituted or unsubstituted $C_1$ to $C_{30}$ hydrocarbon group, or a substituted or unsubstituted $C_1$ to $C_{30}$ hydrocarbon group including a hetero atom; $X_1$, $X_2$, $X_3$, $X_4$, $X_5$ and $X_6$ are each independently an oxygen atom (O), a sulfur atom (S), or NH; and $Y_1$, $Y_2$ and $Y_3$ are each independently a substituted or unsubstituted $C_1$ to $C_{30}$ hydrocarbon group, or a substituted or unsubstituted $C_1$ to $C_{30}$ hydrocarbon group including a hetero atom.

In an example embodiment, $A_1$ may be phosphorus.

In an example embodiment, $R_1$, $R_2$, $R_3$ and $R_4$ may be each independently a substituted or unsubstituted benzene group, or a $C_1$ to $C_{10}$ alkyl group.

In an example embodiment, $X_1$, $X_2$, $X_3$, $X_4$, $X_5$ and $X_6$ may be an oxygen atom (O).

In an example embodiment, $Y_1$, $Y_2$ and $Y_3$ may be each independently a substituted or unsubstituted benzene compound, or a substituted or unsubstituted naphthalene compound.

In an example embodiment, the curing accelerator may include at least one of compounds represented by Formulae 1a to 1f:

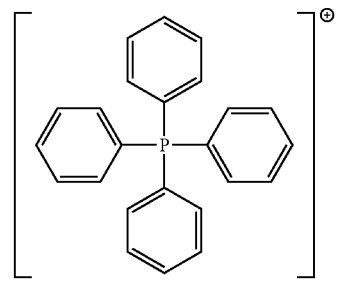

[Formula 1a]

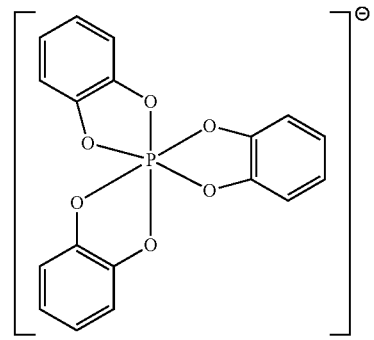

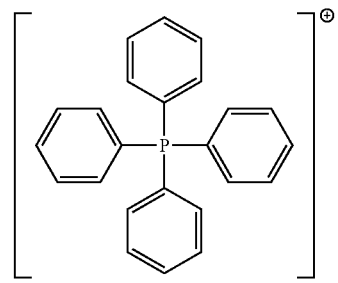

[Formula 1b]

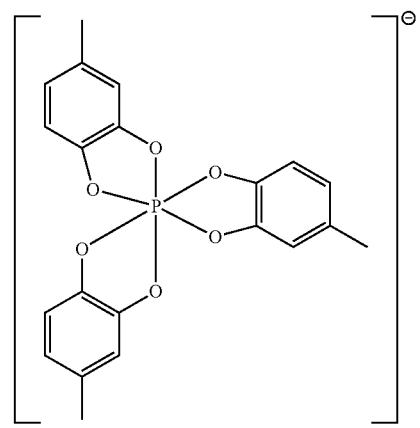

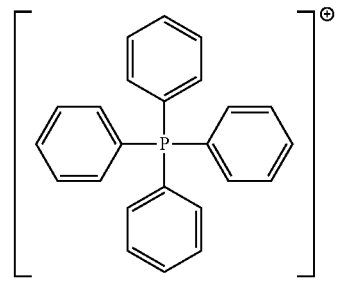

[Formula 1c]

-continued

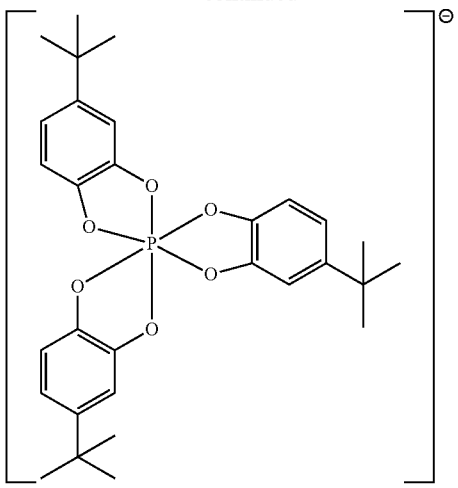

[Formula 1d]

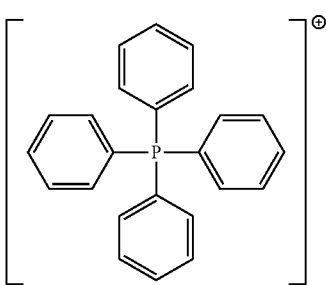

[Formula 1e]

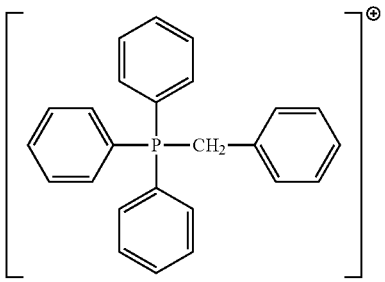

-continued

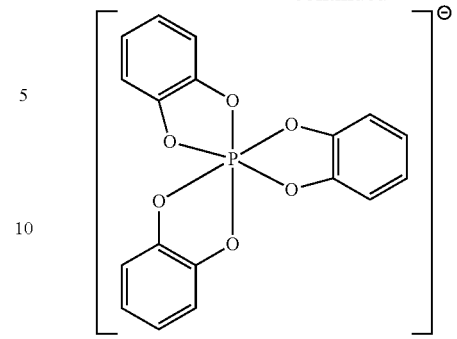

[Formula 1f]

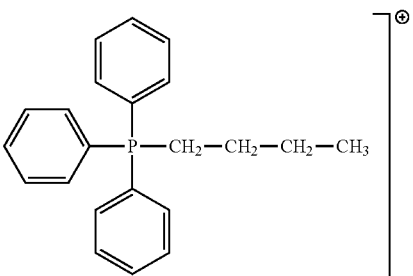

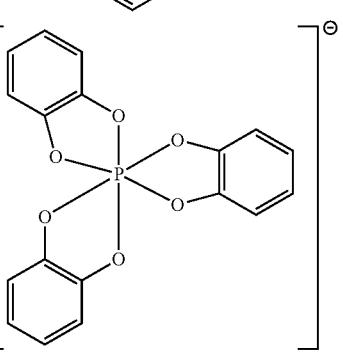

In an example embodiment, the epoxy resin may be present in an amount of about 1% by weight (wt %) to about 20 wt %, the curing agent may be present in an amount of about 1 wt % to about 20 wt %, the curing accelerator may be present in an amount of about 0.001 wt % to about 2 wt %, and the inorganic filler may be present in an amount of about 70 wt % to about 95 wt %.

In an example embodiment, the epoxy resin may include at least one of epoxy resins obtained by epoxidation of a condensate of phenol or alkyl phenol and hydroxybenzaldehyde, phenol novolac type epoxy resins, cresol novolac type epoxy resins, polyfunctional type epoxy resins, naphthol novolac type epoxy resins, novolac type epoxy resins of bisphenol A/bisphenol F/bisphenol AD, glycidyl ethers of bisphenol A/bisphenol F/bisphenol AD, bis-hydroxybiphenyl epoxy resins, dicyclopentadiene epoxy resins, biphenyl type epoxy resins, multi-aromatic modified epoxy resins, bisphenol A type epoxy resins, ortho-cresol novolac type epoxy resins, phenol aralkyl type epoxy resins, and naphthalene epoxy resins.

In an example embodiment, the curing agent may include at least one of phenol aralkyl type resins, xylok type resins, phenol novolac type resins, cresol novolac type resins, naphthol type resins, terpene type resins, polyfunctional type resins, multi-aromatic resins, dicyclopentadiene resins, terpene modified resins, dicyclopentadiene modified phenolic resins, novolac type phenolic resins synthesized from bisphenol A and resol, multivalent phenolic compounds including tris(hydroxyphenyl)methane and dihydroxybiphenyl, acid anhydrides including maleic anhydride and phthalic anhydride, meta-phenylenediamine, diaminodiphenylmethane, and diaminodiphenylsulfone.

In an example embodiment, a composition ratio (equivalent weight of epoxy groups of the epoxy resin to equivalent weight of the phenolic hydroxyl group or amino group included in the curing agent) of the epoxy resin to the curing agent may range from about 0.5:about 1 to about 2:about 1.

In an example embodiment, the inorganic filler may include at least one of fused silica, crystalline silica, calcium carbonate, magnesium carbonate, alumina, magnesia, clay, talc, calcium silicate, titanium oxide, antimony oxide, and glass fibers.

In an example embodiment, the epoxy resin composition may further include colorants, coupling agents, release agents, stress relievers, cross-linking promoters, leveling agents, and flame-retardants.

Another embodiment is directed to a semiconductor device encapsulated using an epoxy resin composition according to an embodiment.

DETAILED DESCRIPTION

Example embodiments will now be described more fully hereinafter; however, they may be embodied in different forms and should not be construed as limited to the embodiments set forth herein. Rather, these embodiments are provided so that this disclosure will be thorough and complete, and will fully convey example implementations to those skilled in the art.

An epoxy resin composition according to an example embodiment includes an epoxy resin, a curing agent, a curing accelerator and an inorganic filler. The epoxy resin composition may be useful for, e.g., encapsulation of semiconductor diodes.

Epoxy Resin

According to the present example embodiment, a general epoxy resin used in preparation of epoxy resin compositions for encapsulation of semiconductor diodes may be used. For example, a epoxy resin having at least two epoxy groups may be used, and may include at least one of monomers, oligomers and polymers.

Examples of the epoxy resin include epoxy resins obtained by epoxidation of a condensate of phenol or alkyl phenol and hydroxybenzaldehyde, phenol novolac type epoxy resin, cresol novolac type epoxy resin, polyfunctional type epoxy resin, naphthol novolac type epoxy resins, novolac type epoxy resins of bisphenol A/bisphenol F/bisphenol AD, glycidyl ethers of bisphenol A/bisphenol F/bisphenol AD, bis-hydroxybiphenyl epoxy resin, dicyclopentadiene epoxy resin, biphenyl type epoxy resin, multi-aromatic modified epoxy resin, bisphenol A type epoxy resin, ortho-cresol novolac type epoxy resin, phenol aralkyl type epoxy resin, naphthalene epoxy resins, mixtures thereof, etc.

A phenol aralkyl type epoxy resin of a novolac structure including biphenyl derivatives represented by Formula 2, a biphenyl type epoxy resin represented by Formula 3, a xylok type epoxy resin represented by Formula 4, and a polyfunctional epoxy resin including a naphthalene skeleton represented by Formula 5, used alone or in combination thereof, may provide an epoxy resin composition exhibiting excellent mechanical properties.

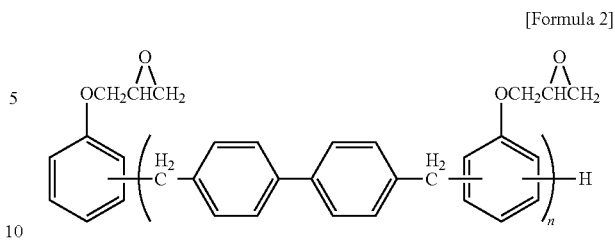

[Formula 2]

wherein an average value of n is 1 to 7.

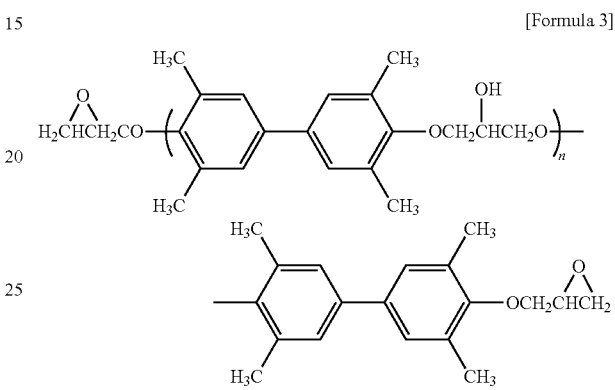

[Formula 3]

wherein an average value of n is 0 to 7.

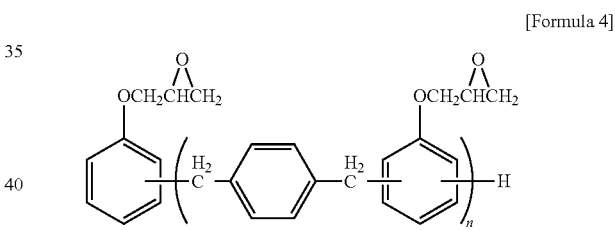

[Formula 4]

wherein an average value of n is 1 to 7.

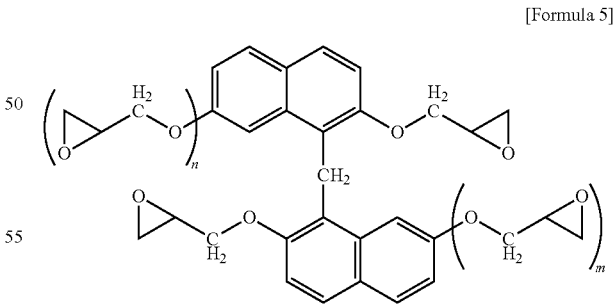

[Formula 5]

wherein average values of m and n are each independently 0 to 6.

In an example embodiment, the epoxy resin may also be used as an adduct compound prepared by pre-reaction, such as melt master batch reaction, of the epoxy resin with the curing agent, the curing accelerator and, optionally, other additives, such as release agents, coupling agents and the like.

In an example embodiment, the epoxy resin is present in an amount of about 1 wt % to about 20 wt %, e.g., about 1 wt % to about 13 wt % or about 1.2 wt % to about 10 wt %, in the epoxy resin composition. Within this range, the epoxy resin composition may exhibit excellent properties in terms of room temperature storage stability, flowability, curing properties, and the like.

Curing Agent

According to the present example embodiment, a general curing agent used in epoxy resin compositions for encapsulation of semiconductor diodes may be used. For example, a curing agent having at least two phenolic hydroxyl groups or amino groups may be used, and may include at least one of monomers, oligomers and polymers.

Examples of the curing agent include phenol aralkyl type resins, xylok type resins, phenol novolac type resins, cresol novolac type resins, naphthol type resins, terpene type resins, polyfunctional type resins, multi-aromatic resins, dicyclopentadiene resins, terpene modified resins, dicyclopentadiene modified phenolic resins, novolac type phenolic resins synthesized from bisphenol A and resol, multivalent phenolic compounds including tris(hydroxyphenyl)methane and dihydroxybiphenyl, acid anhydride including maleic anhydride and phthalic anhydride, aromatic amines such as meta-phenylenediamine, diaminodiphenylmethane, diaminodiphenylsulfone and the like, mixtures thereof, etc.

The curing agent may include at least one of phenol aralkyl type phenolic resins, having a biphenyl skeleton represented by Formula 6 and xylok type phenolic resins represented by Formula 7:

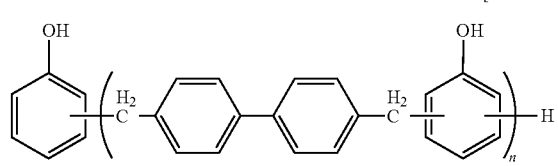

[Formula 6]

wherein an average value of n is an integer from 1 to 7,

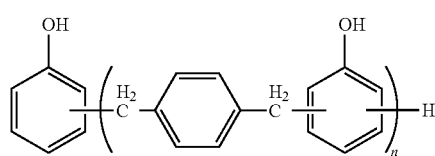

[Formula 7]

wherein an average value of n is an integer from 1 to 7.

In an example embodiment, the curing agent may include the aforementioned curing agent compounds alone or in combination thereof. For example, the curing agent may also be used as an adduct compound prepared by pre-reaction, such as melt master batch reaction, of the curing agent with the epoxy resin, the curing accelerator, other additives, etc.

In an example embodiment, the curing agent has a softening point from about 50° C. to about 100° C., e.g., from about 60° C. to about 90° C. Within this range, the epoxy resin may exhibit appropriate viscosity without deterioration in flowability.

In an implementation, the phenolic hydroxyl or amino groups included in the curing agent may have an equivalent weight of about 90 g/eq to about 300 g/eq.

In an example embodiment, the curing agent is present in an amount of about 1 wt % to about 20 wt %, e.g., 1.5 wt % to about 10 wt % or 2 wt % to about 8 wt %. Within this range, excessive generation of unreacted epoxy groups and unreacted phenolic hydroxyl or amino groups may be prevented, which may help improve reliability of the epoxy resin composition.

In an implementation, a composition ratio (equivalent weight of epoxy groups of the epoxy resin to equivalent weight of phenolic hydroxyl groups or amino groups included in the curing agent) of the epoxy resin to the curing agent is about 0.5:about 1 to about 2:about 1, e.g., about 0.8:about 1 to about 1.6:about 1. Within this range, the epoxy resin composition may secure flowability without retarding curing time.

Curing Accelerator

According to the present example embodiment, the curing accelerator promotes reaction of the epoxy resin and the curing agent, and includes a 4-valent ammonium salt or a 4-valent phosphonium salt represented by Formula 1:

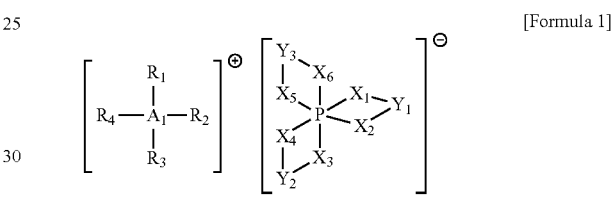

[Formula 1]

wherein $A_1$ is nitrogen (N) or phosphorus (P), e.g., phosphorus (P); $R_1$, $R_2$, $R_3$ and $R_4$ are each independently a substituted or unsubstituted $C_1$ to $C_{30}$, e.g., $C_1$ to $C_{12}$ hydrocarbon group, or a substituted or unsubstituted $C_1$ to $C_{30}$, e.g., $C_1$ to $C_{12}$ hydrocarbon group including a hetero atom or a substituted or unsubstituted benzene group, or $C_1$ to $C_{10}$ alkyl group; $X_1$, $X_2$, $X_3$, $X_4$, $X_5$ and $X_6$ are each independently an oxygen atom (O), a sulfur atom (S) or NH, e.g., an oxygen atom (O); and $Y_1$, $Y_2$ and $Y_3$ are each independently a substituted or unsubstituted $C_1$ to $C_{30}$, e.g., $C_1$ to $C_{12}$ hydrocarbon group, or a substituted or unsubstituted $C_1$ to $C_{30}$, e.g., $C_1$ to $C_{12}$ hydrocarbon group including a hetero atom, or each independently a substituted or unsubstituted benzene group, or a substituted or unsubstituted naphthalene group.

As used herein, the term "substituted" means that a hydrogen atom is substituted with a substituent such as a halogen atom, a $C_1$ to $C_{10}$ alkyl group, a $C_1$ to $C_{10}$ haloalkyl group, a $C_6$ to $C_{10}$ aryl group, a $C_1$ to $C_{10}$ alkoxy group, a $C_2$ to $C_{10}$ carbonyl group, or combinations thereof. In an implementation, unless otherwise stated, the term "alkyl group" refers to a linear, branched or cyclic alkyl group. Further, unless stated otherwise, the term "hydrocarbon group" means a saturated or unsaturated linear, branched or cyclic hydrocarbon group, in which a "branched" type hydrocarbon group may have two or more carbon atoms, a "cyclic" hydrocarbon group may have four or more carbon atoms, and the "hetero atom" includes at least one of an oxygen atom (O), a sulfur atom (S) and a nitrogen atom (N).

In an example embodiment, the curing accelerator may include at least one of compounds represented by Formulae 1a to 1f:

[Formula 1a]
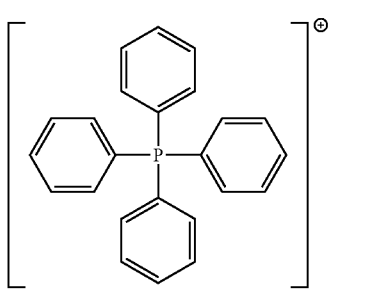
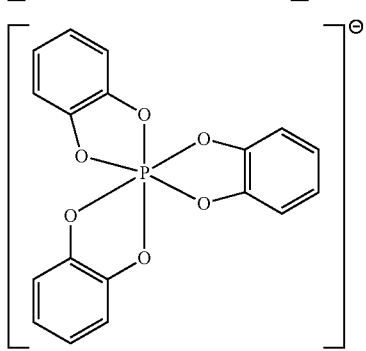
[Formula 1b]
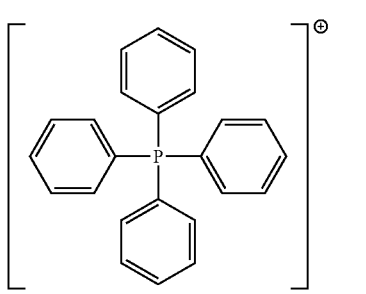
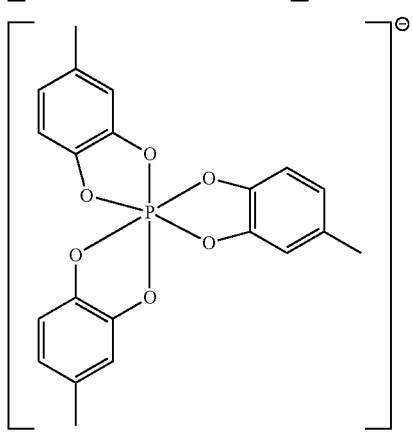
[Formula 1c]
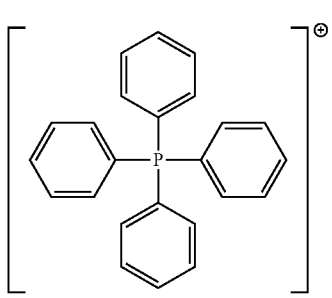
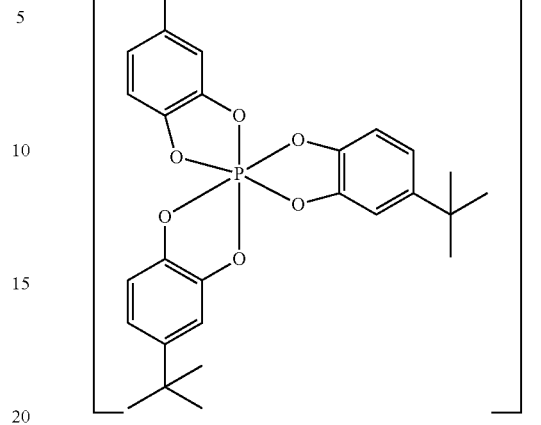
[Formula 1d]
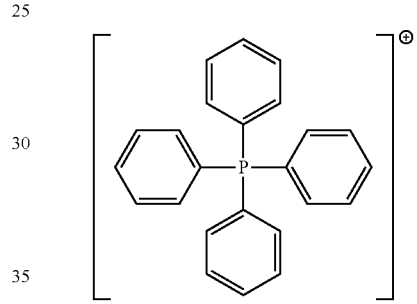
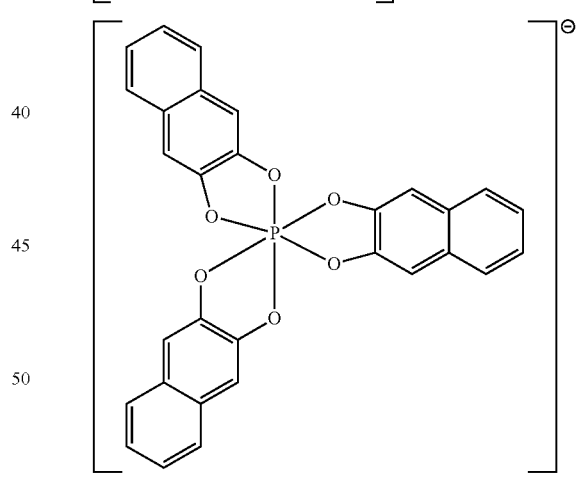
[Formula 1e]
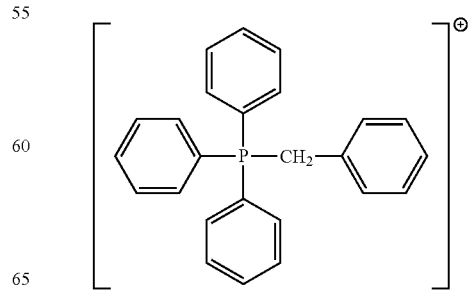

-continued

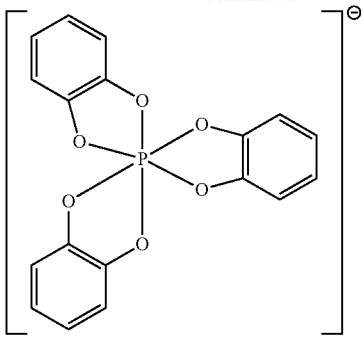

[Formula 1f]

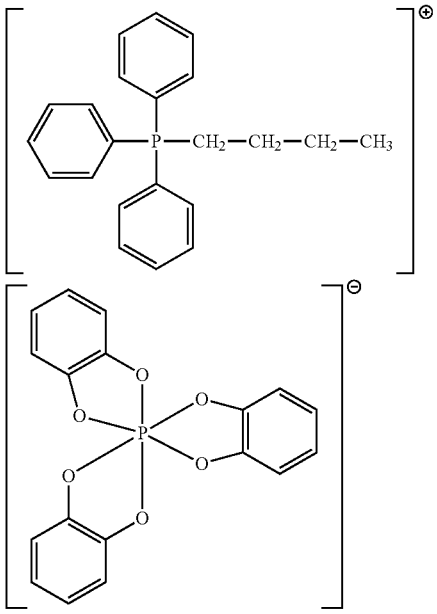

The 4-valent ammonium salt or 4-valent phosphonium salt may be prepared by a general method for preparing phosphonium salts. For example, as disclosed in the following preparative examples, an ammonium salt including an anion unit of Formula 1 may be prepared using triethylamine (TEA) and the like, and may then be dissolved in an alcohol, such as methanol, and the like. Then, an alkaline solution, such as a sodium hydroxide solution or the like, may be added to the alcohol within which the ammonium salt is dissolved, and halogenated 4-valent ammonium or halogenated 4-valent phosphonium corresponding to a 4-valent ammonium cation or 4-valent phosphonium cation of Formula 1 dissolved in the alcohol, such as methanol and the like, may be added thereto and allowed to stand for about 30 minutes. Then, the resulting material may be added to distilled water to form precipitates, which in turn may be dried, thereby preparing the 4-valent ammonium salt or 4-valent phosphonium salt.

The curing accelerator represented by Formula 1 is a salt of the 4-valent ammonium or 4-valent phosphonium, and may exhibit excellent room temperature storage stability (at 25° C., 50% RH), sufficient flowability upon molding, and excellent curing properties such as curing strength.

In an implementation, the curing accelerator may be used together with at least one of tertiary amine, organo-metallic compounds, organic phosphorus compounds, imidazole compounds, boron compounds, and the like, and may be used in an adduct form prepared by pre-reaction with the epoxy resin and/or the curing agent.

In an example embodiment, the curing accelerator is present in a total amount of about 0.001 wt % to about 2 wt %, e.g., about 0.001 wt % to about 1.5 wt % or about 0.01 wt % to about 1 wt %, in the epoxy resin composition. Within this range, the epoxy resin composition may exhibit excellent room temperature storage stability, curing reaction time may not be delayed, and flowability of the composition may be secured.

Inorganic Filler

According to the present example embodiment, the inorganic filler may improve mechanical properties of the epoxy resin composition and lower stress, and may include an inorganic filler generally used for epoxy resin compositions for encapsulation of semiconductor diodes. Examples of the inorganic filler include fused silica, crystalline silica, calcium carbonate, magnesium carbonate, alumina, magnesia, clay, talc, calcium silicate, titanium oxide, antimony oxide, glass fibers, and the like. These may be used alone or in combination thereof.

The inorganic filler may include fused silica having a low coefficient of linear expansion, which may help lower stress. The fused silica refers to amorphous silica having a specific gravity of about 2.3 or less, and may be prepared by melting crystalline silica or may include amorphous silica synthesized from various raw materials.

The inorganic filler may have various shapes and/or particle size. In an implementation, the inorganic filler may have an average particle size from about 0.001 μm to about 30 μm. The inorganic filler may include spherical fused silica having an average particle size from about 0.005 μm to about 28 μm. The inorganic filler may include a mixture of spherical fused silica having different particle sizes. For example, the inorganic filler may be composed of a mixture of about 50 wt % to about 99 wt % of spherical fused silica having an average particle size from about 5 μm to about 30 μm and about 1 wt % to about 50 wt % of spherical fused silica having an average particle size from about 0.001 μm to about 1 μm. In an implementation, the inorganic filler may have a maximum particle size adjusted to one of about 45 μm, about 55 μm and about 75 μm depending upon use.

In an implementation, the inorganic filler may be used after surface treatment thereof with a coupling agent such as epoxy silane, aminosilane, mercaptosilane, alkyl silane, alkoxy silane, mixtures thereof, etc.

The inorganic filler may be included at an ratio determined with reference to properties of the epoxy resin composition, such as moldability, low stress properties, high-temperature strength, and the like. For example, the inorganic filler may be present in an amount of about 70 wt % to about 95 wt %, e.g., about 75 wt % to about 94 wt % or about 82 wt % to about 92 wt %, in the epoxy resin composition. Within this range, the epoxy resin composition may exhibit excellent properties in terms of flexural integrity, package reliability, flowability, and moldability.

Additives

According to the present example embodiment, the epoxy resin composition may include an additive. Example additives may be, e.g., colorants, coupling agents, release agents, stress relievers, cross-linking promoters, leveling agents, flame retardants, and the like.

The colorant may include carbon black, organic or inorganic dyes, and the like.

The coupling agent may include a silane coupling agent. The silane coupling agent may include at least one of epoxy silane, aminosilane, mercaptosilane, alkyl silane, alkoxy silane, and the like.

The release agent may include at least one of paraffin wax, ester wax, higher fatty acids, higher fatty acid metal salts, natural fatty acids, natural fatty acid metal salts, and the like.

The stress reliever may include at least one of modified silicone oil, silicone elastomers, silicone powder, silicone resins, and the like.

The flame retardant may include a non-halogen (organic or inorganic) flame retardant. The non-halogen flame retardant may include at least one of phosphazene, zinc borate, aluminum hydroxide, magnesium hydroxide, and the like.

The additives may be present in an amount of about 15 wt % or less, e.g., about 0.1 wt % to about 5.5 wt %, in the epoxy resin composition. For example, the flame retardancy of the epoxy resin composition may be varied depending upon the amount of the inorganic filler, type of the curing agent, and the like, and the epoxy resin composition may include the flame retardant at an appropriate ratio depending on flame retardancy thereof. For example, the flame retardant may be present in an amount of about 10 wt % or less, e.g., about 0.01 wt % to about 8 wt % or about 0.1 wt % to about 5 wt %, in the epoxy resin composition.

An example of a method for preparing the epoxy resin composition according to an embodiment may include uniformly mixing the respective components of the resin composition using a Henschel or Lödige mixer, and the mixture may be melted and kneaded at temperatures from about 90° C. to about 120° C. using a roll mill or kneader, followed by cooling and pulverization, thereby preparing the epoxy resin composition.

According to an example embodiment, a semiconductor device is encapsulated using the epoxy resin composition according to an embodiment. For encapsulation of a semiconductor device using the epoxy resin composition, low-pressure transfer molding, compression molding, injection molding, cast molding, and the like may be utilized. For example, low-pressure transfer molding may be used. Using these molding methods, a semiconductor device, which may include a copper lead frame, an iron lead frame, a lead frame formed by pre-plating the copper or iron lead frame with at least one of nickel, copper and palladium, an organic laminate frame, and the like, may be prepared.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

EXAMPLES

Preparative Example 1: Preparation of 4-Valent Phosphonium Salt Represented by Formula 1a In a 1 L round-bottom flask, 100 g of catechol, 200 mL of dichloromethane (DCM) and 85 mL of triethylamine were vigorously mixed until these components were completely dissolved. A solution prepared by adding 63 mL of chlorodiphenylphosphate to 200 mL of DCM was added dropwise to the prepared solution. After further reaction at room temperature for 3 hours, solid products were isolated via filtration, washed with water and dried, thereby obtaining 125 g of a white solid (p1) as an ammonium salt. Next, in a 1 L round-bottom flask to which 50 g of p1 and 100 mL of MeOH were added, 20 mL of a 5 M NaOH aqueous solution was added to the flask while mixing p1 and MeOH, followed by performing reaction for 30 minutes at a reaction temperature of 60° C. After p1 was completely dissolved, a solution prepared by dissolving 46 g of tetraphenylphosphonium bromide in 100 mL of MeOH was added dropwise to the mixture, followed by further performing reaction for 2 hours. Then, the resultant was cooled to room temperature, and solids created by dropwise addition of 500 mL of distilled water thereto were isolated via filtration, washed with water and dried, thereby obtaining 61 g of a 4-valent phosphonium salt, represented by Formula 1a, as a white solid.

[Formula 1a]

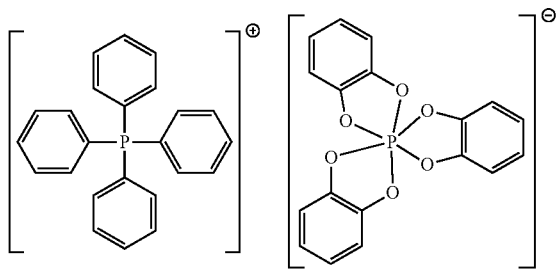

Preparative Example 2: Preparation of 4-Valent Phosphonium Salt Represented by Formula 1b 61 g of a 4-valent phosphonium salt, represented by Formula 1b, as a white solid, was obtained in the same manner as in Preparative Example 1 except that after 105 g of a white solid (p2) was obtained using 115 g of 4-methylcatechol instead of 100 g of catechol, p2 was used instead of p1, and 42 g of tetraphenylphosphonium bromide was used instead of 46 g of tetraphenylphosphonium bromide.

[Formula 1b]

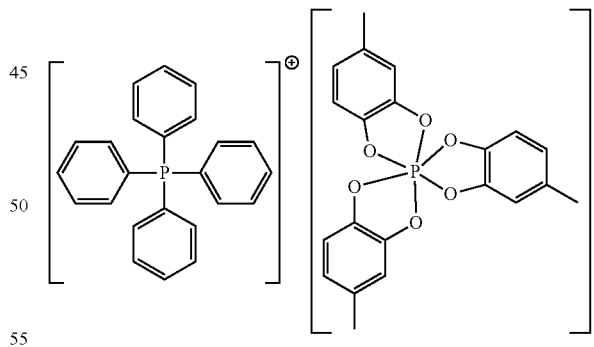

Preparative Example 3: Preparation of 4-Valent Phosphonium Salt Represented by Formula 1c 32 g of a 4-valent phosphonium salt, represented by Formula 1c, as a white solid, was obtained in the same manner as in Preparative Example 1 except that after 116 g of a white solid (p3) was obtained using 151 g of 4-tert-butylcatechol instead of 100 g of catechol, p3 was used instead of p1, 16 mL of the 5 M aqueous NaOH solution was used instead of 20 mL thereof, and 34 g of tetraphenylphosphonium bromide was used instead of 46 g thereof.

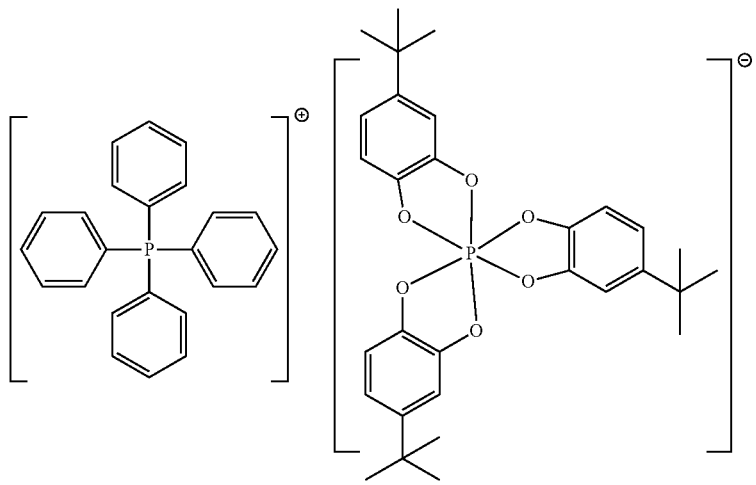

[Formula 1c]

Preparative Example 4: Preparation of 4-Valent Phosphonium Salt Represented by Formula 1d 49 g of a 4-valent phosphonium salt, represented by Formula 1d, as a white solid, was obtained in the same manner as in Preparative Example 1 except that after 166 g of a white solid (p4) was obtained using 145 g of 2,3-dihydroxynaphthalene instead of 100 g of catechol, p4 was used instead of p1, 16.5 mL of the 5 M aqueous NaOH solution was used instead of 20 mL thereof, and 35 g of tetraphenylphosphonium bromide was used instead of 46 g thereof.

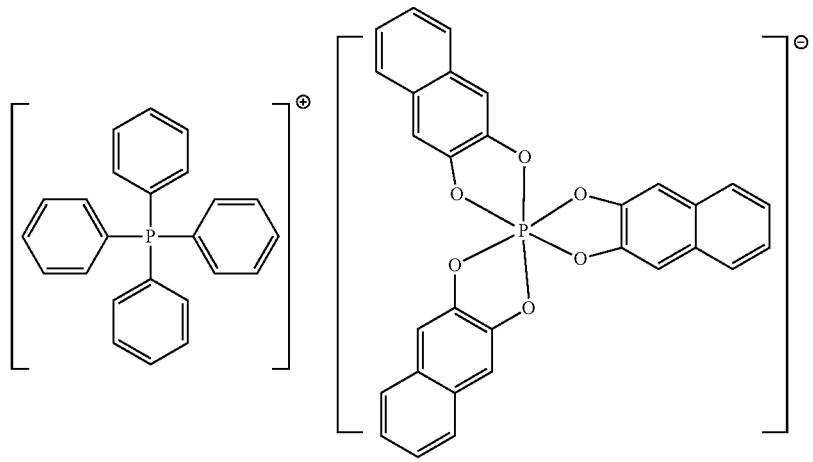

[Formula 1d]

Preparative Example 5: Preparation of 4-Valent Phosphonium Salt Represented by Formula 1e 68 g of a 4-valent phosphonium salt, represented by Formula 1e, as a white solid, was obtained in the same manner as in Preparative Example 1 except that 43 g of benzyltriphenylphosphonium chloride was used instead of 46 g of tetraphenylphosphonium bromide.

[Formula 1e]

Preparative Example 6: Preparation of 4-Valent Phosphonium Salt Represented by Formula 1f 61 g of a 4-valent phosphonium salt, represented by Formula 1e, as a white solid, was obtained in the same manner as in Preparative Example 1 except that 48 g of butyltriphenylphosphonium bromide was used instead of 46 g tetraphenylphosphonium bromide.

[Formula 1f]

Details of components used in the following examples and comparative examples are as follows:

(A) Epoxy Resin

A phenol aralkyl type epoxy resin NC-3000 (Nippon Kayaku Co., Ltd.) was used.

(B) Curing Agent

A xylok type phenolic resin HE100C-10 (Air Water Co., Ltd.) was used.

(C) Curing Accelerator (C1) to (C6): 4-valent phosphonium salts prepared in Preparative Examples 1 to 6 were respectively used in (C1) to (C6).

(C7): Triphenyl phosphine was used.

(C8): An adduct of triphenyl phosphine and 1,4-benzoquinone was used.

(D) Inorganic Filler: A mixture of spherical fused silica having an average particle size of 18 μm and spherical fused silica having an average particle size of 0.5 μm mixed in a ratio of 9:1 (weight ratio) was used.

(E) Coupling Agent (e1) A mixture of mercaptopropyltrimethoxysilane KBM-803 (Shinetsu Co. Ltd.) and (e2) Methyltrimethoxysilane SZ-6070 (Dow Corning chemical Co., Ltd.) was used.

(F) Additives (f1) As a release agent, carnauba wax was used, and (f2) as a colorant, carbon black MA-600 (Matsushita Chemical Co., Ltd.) was used.

Examples 1 to 5 and Comparative Examples 1 to 2

After weighing the respective components according to the composition as listed in Table 1, the components were uniformly mixed, thereby preparing a first composition in a powder state. Next, after melting and kneading at 95° C. using a continuous kneader, the first composition was cooled and pulverized, thereby preparing an epoxy resin composition for encapsulation of semiconductor diodes.

TABLE 1

|     |      | Example |      |      |      |      |      | Comparative Example |      |
|-----|------|---------|------|------|------|------|------|---------------------|------|
|     |      | 1       | 2    | 3    | 4    | 5    | 6    | 1                   | 2    |
| (A) |      | 8.69    | 8.69 | 8.69 | 8.69 | 8.69 | 8.69 | 8.69                | 8.69 |
| (B) |      | 5.01    | 5.01 | 5.01 | 5.01 | 5.01 | 5.01 | 5.01                | 5.01 |
| (C) | C1   | 0.3     | —    | —    | —    | —    | —    | —                   | —    |
|     | C2   | —       | 0.3  | —    | —    | —    | —    | —                   | —    |
|     | C3   | —       | —    | 0.3  | —    | —    | —    | —                   | —    |
|     | C4   | —       | —    | —    | 0.3  | —    | —    | —                   | —    |
|     | C5   | —       | —    | —    | —    | 0.3  | —    | —                   | —    |
|     | C6   | —       | —    | —    | —    | —    | 0.3  | —                   | —    |
|     | C7   | —       | —    | —    | —    | —    | —    | 0.3                 | —    |
|     | C8   | —       | —    | —    | —    | —    | —    | —                   | 0.3  |
| (D) |      | 85      | 85   | 85   | 85   | 85   | 85   | 85                  | 85   |
| (E) | (e1) | 0.2     | 0.2  | 0.2  | 0.2  | 0.2  | 0.2  | 0.2                 | 0.2  |
|     | (e2) | 0.2     | 0.2  | 0.2  | 0.2  | 0.2  | 0.2  | 0.2                 | 0.2  |
| (F) | (f1) | 0.3     | 0.3  | 0.3  | 0.3  | 0.3  | 0.3  | 0.3                 | 0.3  |
|     | (f2) | 0.3     | 0.3  | 0.3  | 0.3  | 0.3  | 0.3  | 0.3                 | 0.3  |

Evaluation of Properties (1) Flowability (unit: inch): Flow length was measured by transfer press molding at 175° C. under a pressure of 70 kgf/cm² using an evaluation mold in accordance with EMMI-1-66. Higher measurement values indicate superior flowability.

(2) Curing shrinkage rate (unit: %): A molded specimen (125 mm×12.6 mm×6.4 mm) was obtained by transfer press molding at 175° C. under a pressure of 70 kgf/cm² using an ASTM mold for preparation of flexural strength specimens. After post mold curing (PMC) of the prepared specimen in an oven at 170° C. to 180° C. for 4 hours, the specimen was cooled, followed by measuring the length of the specimen using calipers. Curing shrinkage rate was calculated by Equation 1:

Curing shrinkage rate=(length of mold at 175° C.−length of specimen)÷(length of mold at 175° C.)×100.

(3) Glass transition temperature (unit: ° C.): Glass transition temperature was measured using a thermomechanical analyzer (TMA). Here, TMA analysis was performed from 25° C. to 300° C. at a heating rate of 10° C. per minute.

(4) Moisture absorption rate (unit: %): A disc-shaped cured specimen having a diameter of 50 mm and a thickness of 1.0 mm was obtained by molding each of the resin compositions prepared in Examples and Comparative Examples at a mold temperature from 170° C. to 180° C., a clamp pressure of 70 kgf/cm², a transfer pressure of 1000 psi, a transfer speed from 0.5 cm/s to 1 cm/s and a curing time of 120 seconds. After post mold curing (PMC) of the specimen in an oven at 170° C. to 180° C. for 4 hours, the specimen was stored at 85° C. and 85% RH for 168 hours, and then, weight change thereof due to moisture absorption was measured. Moisture absorption rate was calculated by Equation 2:

Moisture absorption rate=(weight of specimen after moisture absorption−initial weight of specimen)÷(initial weight of specimen)×100.

(5) Adhesive strength (unit: kgf): A copper metal device having a size suited to a mold for adhesive strength measurement was prepared, and a cured specimen was obtained by molding each of the resin compositions prepared in Examples and Comparative Examples at a mold temperature from 170° C. to 180° C., a clamp pressure of 70 kgf/cm², a transfer pressure of 1000 psi, a transfer speed from 0.5 cm/s to 1 cm/s, and a curing time of 120 seconds. Post mold curing (PMC) of the obtained specimen was performed in an oven at 170° C. to 180° C. for 4 hours. Here, the area in which the epoxy resin composition contacted the specimen was 40±1 mm², and adhesive strength was measured on 12 specimens using a universal testing machine (UTM). Then, an average value was calculated.

(6) Room temperature storage stability (unit: %): After flowability of each epoxy resin composition was measured according to the same method as in (1), the epoxy resin composition was left at 25° C. and 50% RH for 3 days, and then, flowability was measured again. By substituting the measured flowability value into Equation 3, room temperature storage stability was calculated. Here, higher values indicate superior room temperature storage stability.

Room temperature storage stability=(measured flowability after storage at 25° C. and 50% RH for 3 days)÷(measured flowability immediately after preparation)×100. [Equation 3]

(7) Hardness (shore-D): After an epoxy resin composition to be evaluated was cured at 175° C. for each of 50, 60, 70, 60 and 90 seconds using a multi-plunger system (MPS) molding machine, which includes a mold for exposed Thin Quad Flat Package (eTQFP), having a width of 24 mm, a length of 24 mm and a thickness of 1 mm, and including a copper metal device, hardness of the cured product was directly measured on a package of the mold using a Shore type-D hardness tester depending on curing time. Higher values indicate superior degree of curing.

(8) Reliability: After eTQFP for evaluation of hardness (curing time 90 seconds) was dried at 125° C. for 24 hours, a thermal shock test consisting of 5 cycles (1 cycle means that the package is left at −65° C. for 10 minutes, at 25° C. for 10 minutes and at 150° C. for 10 minutes). Then, the package was left under conditions of 85° C. and 60% RH for 168 hours. After preconditioning in which IR reflow at 260° C. for 30 seconds was repeated 3 times, exterior cracking in the package was observed using an optical microscope. Then, peeling of the epoxy resin composition from lead frames was evaluated using scanning acoustic microscopy (C-SAM), which is non-destructive evaluation. Exterior cracking or peeling of the epoxy resin composition from lead frames degrade reliability of the package.

The properties of the epoxy resin compositions prepared in Examples and Comparative Examples were evaluated using the above methods, and measurement results are shown in Table 2.

TABLE 2

| | | | Example | | | | | | Comparative Example | |
|---|---|---|---|---|---|---|---|---|---|---|
| | Evaluation item | | 1 | 2 | 3 | 4 | 5 | 6 | 1 | 2 |
| Basic properties | Flowability (inch) | | 82 | 78 | 86 | 76 | 81 | 81 | 52 | 58 |
| | Curing shrinkage rate (%) | | 0.27 | 0.23 | 0.26 | 0.27 | 0.25 | 0.26 | 0.34 | 0.32 |
| | Glass transition temperature (° C.) | | 125 | 126 | 123 | 124 | 122 | 125 | 121 | 122 |
| | Moisture absorption rate (%) | | 0.25 | 0.25 | 0.24 | 0.25 | 0.22 | 0.24 | 0.25 | 0.26 |
| | Adhesive strength (kgf) | | 75 | 76 | 74 | 77 | 75 | 74 | 72 | 74 |
| | Room temperature storage stability (%) | | 95 | 91 | 95 | 92 | 93 | 93 | 49 | 53 |
| Package evaluation | Hardness depending on curing time (Shore-D) | 60 seconds | 70 | 72 | 71 | 67 | 70 | 71 | 54 | 62 |
| | | 70 seconds | 71 | 72 | 73 | 72 | 73 | 74 | 58 | 65 |
| | | 80 seconds | 74 | 75 | 74 | 73 | 73 | 75 | 64 | 68 |
| | | 90 seconds | 76 | 76 | 74 | 74 | 74 | 76 | 66 | 70 |
| | | 100 seconds | 77 | 78 | 76 | 75 | 76 | 77 | 66 | 70 |
| | Reliability | Number of exterior cracks | 0 | 0 | 0 | 0 | 0 | 0 | 0 | 0 |
| | | Number of cases of peeling | 0 | 0 | 0 | 0 | 0 | 0 | 4 | 2 |

TABLE 2-continued

| Evaluation item | Example | | | | | | Comparative Example | |
|---|---|---|---|---|---|---|---|---|
| | 1 | 2 | 3 | 4 | 5 | 6 | 1 | 2 |
| Number of tested semiconductors | 88 | 88 | 88 | 88 | 88 | 88 | 88 | 88 |

From the results shown in Table 2, it may be seen that the epoxy resin compositions prepared in Examples 1 to 6 exhibited significantly higher flowability and room temperature storage stability, and superior curing strength to those in Comparative Examples 1 and 2. It may be seen that the epoxy resin compositions prepared in Examples 1 to 6 had a relatively low curing shrinkage rate and exhibited a good moisture absorption rate. In reliability evaluation, it may be seen that the epoxy resin compositions prepared in Examples 1 to 6 exhibited crack resistance since no exterior cracking occurred, and exhibited extremely good reliability since no peeling occurred.

By way of summation and review, transfer molding may improve properties and reliability of semiconductor devices by modifying an epoxy resin or a phenolic resin used as a curing agent.

In order to promote curing reaction of a resin, an epoxy resin composition for electric and electronic materials may employ an amine compound, such as a tertiary amine and imidazole, phosphine, phosphonium salts, and the like.

With the trend towards smaller, lighter and higher-performance electronic devices, integration of semiconductors has accelerated every year together with increasing requirement for surface mounting of semiconductor devices, presenting issues that may be difficult to solve. Moreover, materials recently used for packaging of semiconductor devices may require rapid curing for improvement of productivity and preservation safety for improvement of handling upon distribution and storage.

Adducts of triphenyl phosphine and 1,4-benzoquinone may be used as curing accelerators, but these curing accelerators may promote a curing reaction even at relatively low temperatures. Also, curing reaction of an epoxy resin composition may be partially carried out even by heat generated from a mixture when the epoxy resin composition is mixed with other components, or even by heat applied from outside before curing reaction. Moreover, after completion of mixing, the curing reaction may be carried out even when the epoxy resin composition is stored at room temperature.

Such partial curing reaction may cause an increase in viscosity or deterioration in flowability when the epoxy resin composition is liquid, and may alter viscosity when the epoxy resin composition is solid. Moreover, a change of state may not uniformly occur in the epoxy resin composition, and deterioration of moldability may occur together with deterioration in mechanical, electrical, and chemical properties of molded articles occur due to deterioration of flowability when the epoxy resin composition is molded through curing reaction at high temperatures.

The use of curing accelerators may degrade storage stability of the epoxy resin composition. Thus, strict quality management, storage or transport at low temperature, and strict control of molding conditions may be important, and handling may be difficult.

A surface mounting type package may be used in place of a pin insertion type package due to high density mounting in packaging technology of electronic component devices. A surface mounting type package may tend to deteriorate package cracking properties upon soldering, as compared with a pin insertion type package. In surface mounting type packages, such as ICs, LSIs and the like, an occupied volume of diodes in a package my be increased, and the package may be significantly thinner in order to increase mounting density. The surface mounting type package may be exposed to a high temperature of 200° C. or more in a solder reflow process. Thus, moisture and volatile components may rapidly expand and cause cracking of a semiconductor device, when included in the package. Moreover, in a high temperature reflow process, when adhesion of cured products of the epoxy resin composition to the semiconductor diodes, lead frames, and the like inside the semiconductor device is insufficient at an interface therebetween, peeling may occurs at this interface and result in deterioration of moisture resistance.

A semiconductor device produced by packaging semiconductor diodes with the cured product of the epoxy resin composition prepared using an adduct of triphenyl phosphine and 1,4-benzoquinone as a curing accelerator may not exhibit sufficient moisture resistance and crack resistance. A latent curing accelerator (catalyst), which may secure room temperature storage stability of an epoxy resin composition and sufficient flowability while providing crack resistance and moisture resistance may be useful.

As described above, embodiments may provide an epoxy resin composition that may exhibit excellent properties in terms of curing properties, room temperature storage stability, flowability, crack resistance, moisture resistance and the like, and a semiconductor device encapsulated using the same. Embodiments may provide an epoxy resin composition for encapsulation of semiconductor diodes, which may exhibit excellent properties in terms of room temperature storage stability, flowability, curing properties, crack resistance and moisture resistance, and a semiconductor device encapsulated using the same.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. An epoxy resin composition for encapsulating a semiconductor device, comprising:
an epoxy resin; a curing agent; an inorganic filler; and a curing accelerator,
wherein the epoxy resin is present in an amount of about 1 wt % to about 20 wt %, the curing agent is present in an amount of about 1 wt % to about 20 wt %, the curing accelerator is present in an amount of about 0.001 wt % to about 2 wt %, and the inorganic filler is present in an amount of about 70 wt % to about 95 wt %,
wherein the curing accelerator includes one or more compounds represented by Formulae 1a to 1f:

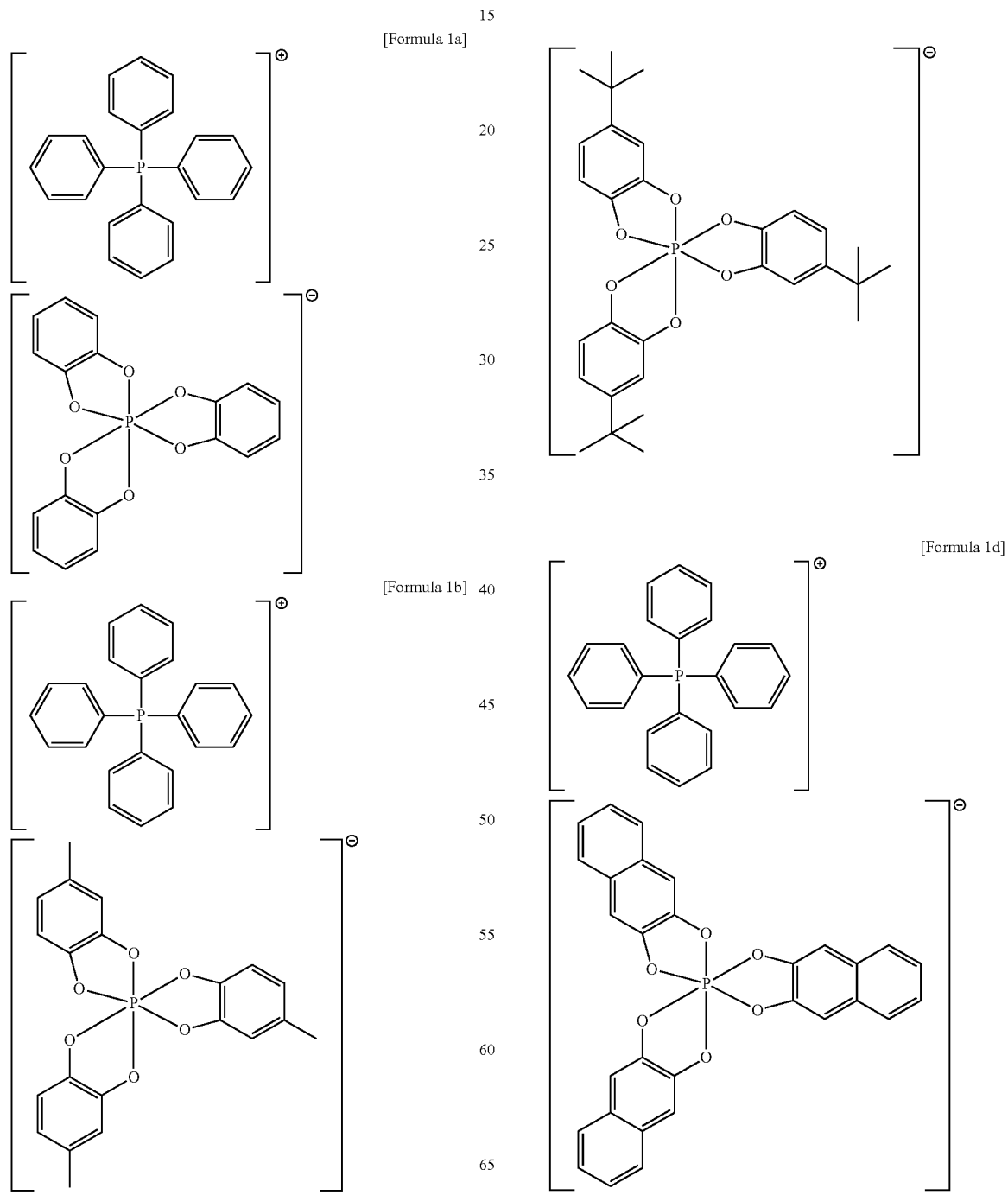

[Formula 1e]

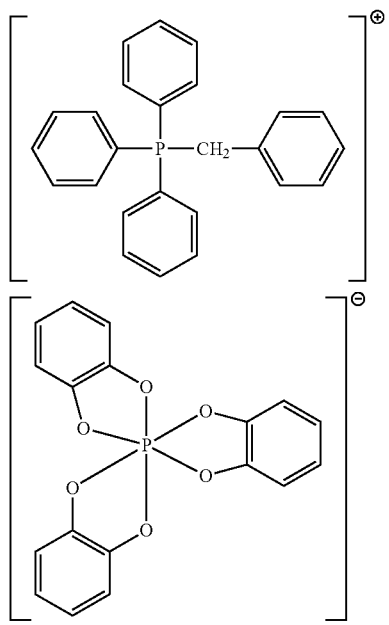

[Formula 1f]

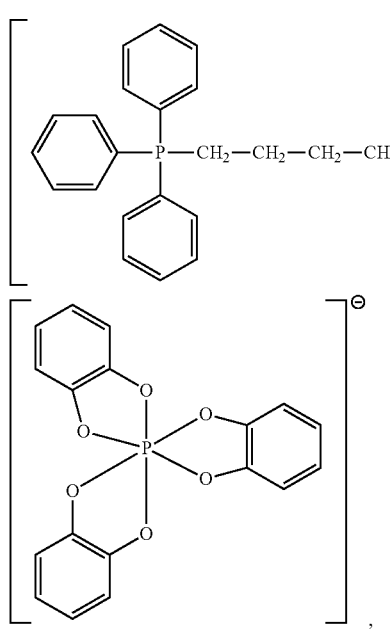

wherein the epoxy resin includes one or more compounds represented by Formulae 2 to 5:

[Formula 2]

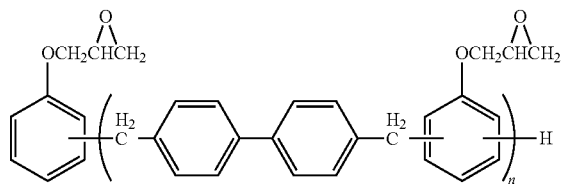

wherein an average value of n is 1 to 7,

[Formula 3]

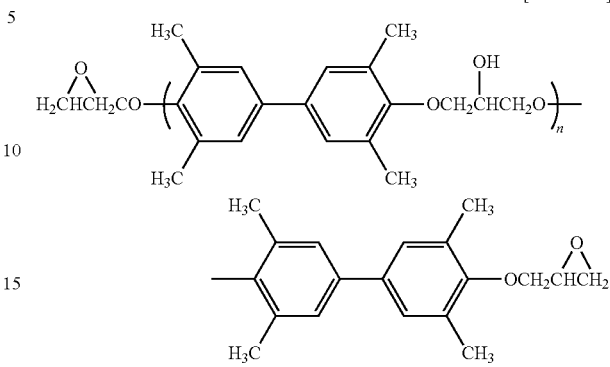

wherein an average value of n is 0 to 7,

[Formula 4]

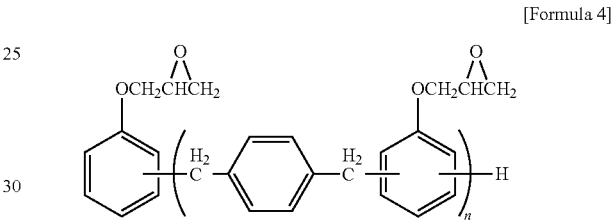

wherein an average value of n is 1 to 7,

[Formula 5]

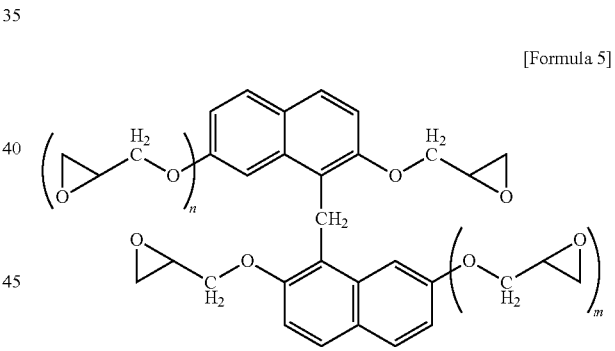

wherein average values of m and n are each independently 0 to 6, and wherein the curing agent includes one or more of Formula 6 and Formula 7:

[Formula 6]

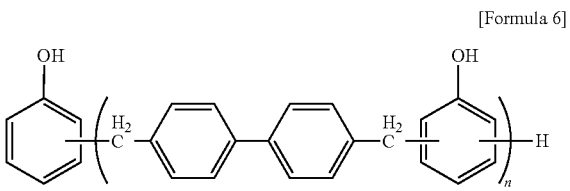

wherein an average value of n is an integer from 1 to 7,

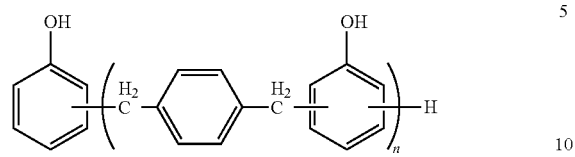
[Formula 7]

wherein an average value of n is an integer from 1 to 7.

2. The epoxy resin composition as claimed to claim 1, wherein a composition ratio of the epoxy resin to the curing agent ranges from about 0.5:about 1 to about 2:about 1, the composition ratio being an equivalent weight of epoxy groups of the epoxy resin to equivalent weight of the phenolic hydroxyl group included in the curing agent.

3. The epoxy resin composition as claimed to claim 1, wherein the inorganic filler includes one or more of fused silica, crystalline silica, calcium carbonate, magnesium carbonate, alumina, magnesia, clay, talc, calcium silicate, titanium oxide, antimony oxide, or glass fibers.

4. The epoxy resin composition as claimed to claim 1, further comprising one or more of a colorant, a coupling agent, a release agent, a stress reliever, a cross-linking promoter, a leveling agent, or a flame-retardant.

5. A semiconductor device encapsulated using the epoxy resin composition as claimed in claim 1.

* * * * *